Figure 1:
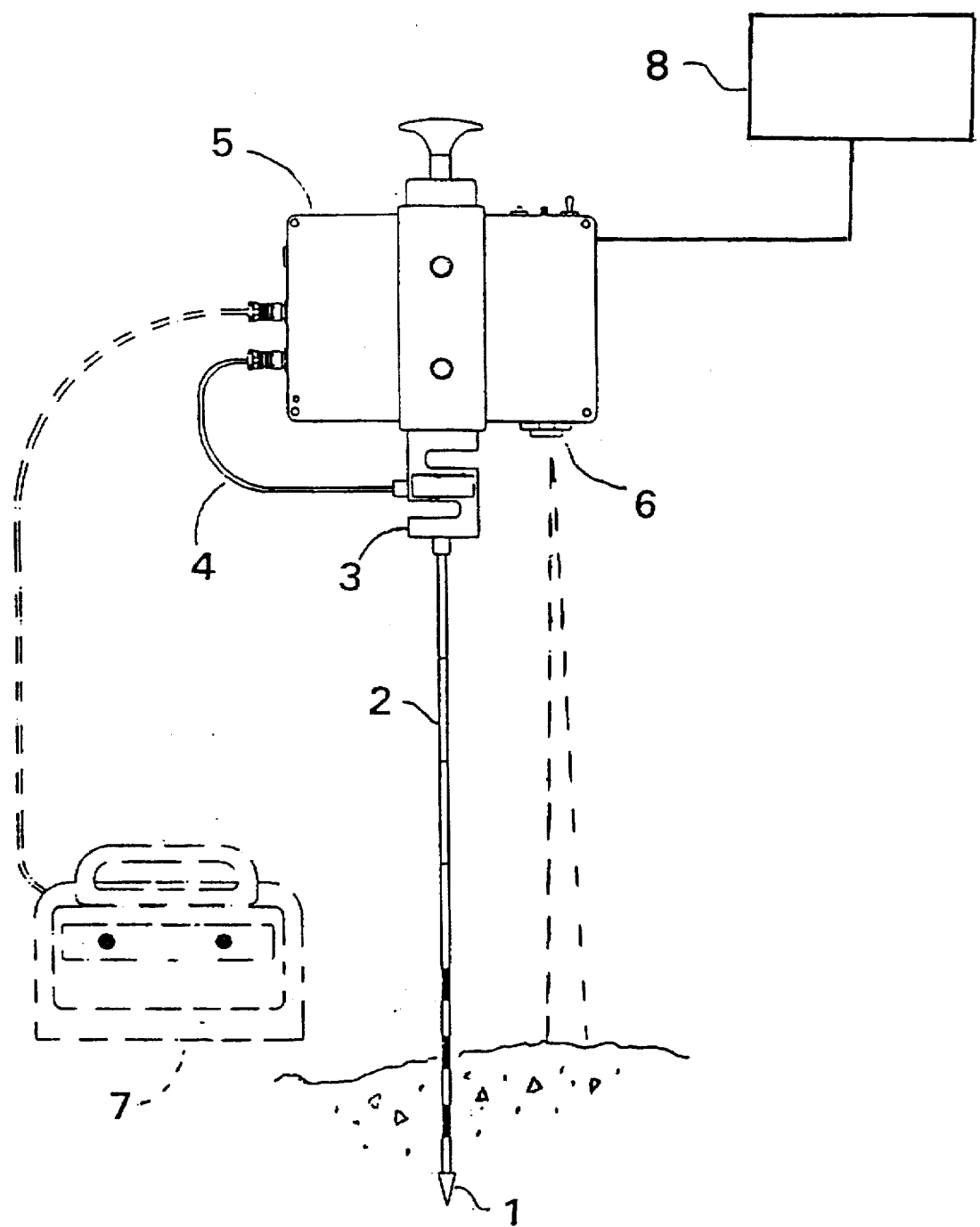

United States Patent [19]
Palmertree et al.

[11] Patent Number: 5,726,349
[45] Date of Patent: Mar. 10, 1998

[54] AUTOMATED CONE PENETROMETER

[75] Inventors: Billy G. Palmertree, Vicksburg, Miss.;
Lewis Bonny Naron, Tallulah, La.;
James H. Robinson, Vicksburg, Miss.

[73] Assignee: United States Army Corps of Engineers As Represented By the Secretary of the Army, Washington, D.C.

[21] Appl. No.: 444,352

[22] Filed: May 18, 1995

[51] Int. Cl.$^6$ .................................................. G01N 3/00
[52] U.S. Cl. ............................................................ 73/84
[58] Field of Search ...................... 73/784, 81, 82, 73/84

[56] References Cited

U.S. PATENT DOCUMENTS

| | | | |
|---|---|---|---|
| 2,130,751 | 9/1938 | Van der Meer | 73/84 |
| 4,061,021 | 12/1977 | Baldwin et al. | 73/84 |
| 4,332,160 | 6/1982 | Baragar et al. | 73/84 |
| 4,382,384 | 5/1983 | Mitchell et al. | 73/84 |
| 4,649,741 | 3/1987 | Strom | 73/84 |
| 4,852,397 | 8/1989 | Haggag | 73/82 |
| 5,275,513 | 1/1994 | Geary et al. | |

*Primary Examiner*—Robert Raevis
*Attorney, Agent, or Firm*—Luther A. Marsh

[57] ABSTRACT

A compact, portable cone penetrometer for determining the shear resistance of soil measures the compressive force on the penetrometer in penetrating the ground by a load cell and the depth of penetration of the ground by an ultrasonic proximity sensor. The outputs of the load cell and the proximity sensor are stored in the memory of a data logger/processor, from which the field data may later be transferred to a digital computer for averaging and tabulating of the data.

9 Claims, 1 Drawing Sheet

AUTOMATED CONE PENETROMETER

GOVERNMENT INTEREST

The invention described herein may be manufactured, licensed, and used by or for governmental purposes without the payment of any royalties thereon.

I. BACKGROUND OF THE INVENTION

1. Field of Invention

This invention relates generally to a cone penetrometer for determining the shear resistance of soil, and in particular to a cone penetrometer in which shear resistance of soil and depth below the ground are measured and the measurement data logged automatically in a field instrument, from which such data may later be transferred to a digital computer for data analysis.

2. Prior Art

Cone penetrometers are used to determine the shear resistance of soil at various depths below the surface. Soil shear resistance measurements may, for example, dictate whether a particular structure can be built at a chosen location, or it may influence the design of building foundations. Cone penetrometers are forced into the ground and the resistance of the ground to penetration and rotation are determined.

U.S. Pat. No. 4,332,160 discloses a penetrometer which is driven into the ground by a drill rig, having a load cell which provides an electrical signal output indicating the mechanical force exerted in penetrating the soil. U.S. Pat. No. 4,382,384 discloses a penetrometer having a cone tip, a friction sleeve, and a microphone in the tip of the penetrometer. The force on the cone tip and the friction force along the friction sleeve are independently measured and recorded, and the sound generated by the microphone during soil penetration is separately recorded on magnetic tape. U.S. Pat. No. 4,649,741 discloses a penetrometer having a rotating shaft with vanes mounted on the end. A torque motor rotates the penetrometer shaft and vanes in a predrilled shaft and a torque cell measures the torque required to rotate the penetrometer shaft at various depth below the surface of the ground.

A light-weight, portable, hand-held penetrometer used by the U.S. military services consists of a rod, about ⅜ inches in diameter and about 19 inches long, having a 30-degree cone at one point having a predetermined surface area, e.g. 0.2 or 0.5 square inches, and a ring whose deflection under mechanical compression gives an indication of the force being applied to the penetrometer in penetrating the ground. The deflection of the ring is read on a dial, which is directly calibrated in pounds of applied force. The depth of penetration into the ground is read on the side of the penetrometer rod, which has markings at 1" intervals.

The conventional system of gathering cone penetrometer data with this equipment requires two people and is time-consuming. One person pushes the cone into the soil and reads the dial indicating the pounds of force exerted on the penetrometer. The other person reads the depth of penetration and records the dial readings, the depth of penetration, the location, and the time of measurement on a form. After the field measurements have been completed, the field records are taken to the office and the field readings for a given location are averaged and tabulated as required.

II. SUMMARY OF THE INVENTION

It has now been determined that the cumbersome method of gathering, recording, averaging, and storing of cone penetrometer data can be speeded up, made more accurate, and carried out by one rather than two persons.

In the cone penetrometer of this invention, the deflection ring and dial for reading the penetrating force of the conventional penetrometer is replaced by a load cell having an electrical resistance which is variable with the compressive force transmitted to the load cell by the penetrometer rod. A resistance bridge is typically used to generate a voltage signal commensurate with the load upon the load cell.

The gradations on the side of the penetrometer rod for determining the depth of penetration into the soil are replaced by an ultrasonic proximity sensor, an ultrasonic emitter/receiver directing an high-frequency sound signal at the ground and receiving a reflected sound signal an instance later. From the time delay between the emitted and reflected ultrasonic signal and the velocity of sound in air, about 330 m/sec, the distance between the ultrasonic emitter and the ground is determined. This distance, subtracted from the length of the penetrometer rod, yields the depth of cone penetration into the soil. The signal outputs may be electrical current or voltage.

The outputs of the load cell and the ultrasonic device are recorded in a data logger/processor which is part of the penetrometer. Analog signals are converted to digital form. digital data are processed into appropriate units of measurement and stored in the memory of the data logger/processor during field operations. Site identification, map coordinates, and the date and time of the measurement may also be entered via a keyboard. Such data are later retrieved into a personal computer, which has appropriate program instructions for averaging and tabulating field data as required.

III. BRIEF DESCRIPTION OF THE DRAWING

FIG. 1 depicts a schematic embodiment of this invention.

IV. DETAILED DESCRIPTION OF THE INVENTION

With reference to FIG. 1, a cone 1 having a cone angle of 30 degrees is attached to the lower end of a rod 2. The upper end of the rod is connected to a load cell 3 which provides an electric analog signal at its terminals that is commensurate with the compressive force being exerted on the load cell as the cone 1 and the rod 2 are being forced into the ground. A load cell for this application is provided by Interface, Inc., of Scottsdale, Ariz., model number SSM-AJ-500. This unit has a resistance bridge which, with an input voltage of about 5 volts, provides an output range of 0–10 millivolts for a range of compressive force of about 0–250 pounds. This voltage signal is transmitted by the wires 4 to a data logger 5.

An ultrasonic emitter/receiver 6 emits high-frequency sound signals towards the ground and receives reflected signals from the ground. Ultrasonic proximity sensors for this application are provided, for example, by Electro Corporation, of Sarasota, Fla. Their signal outputs may be electrical current, such as 4–20 milliamperes for 4–30 inches, or 0–5 volts direct current for 0–30 inches. The current or voltage output signals, which are commensurate to the distance between the emitter and the ground, are transmitted to the data logger/processor 5.

The data logger/processor 5 is a data storage and computation device such as, for instance, a Tattletale Model 2B, supplied by the Onset Computer Company, having about 230,000 bytes of program and digital memory capacity and a DC power supply 7 (9–20 volts). Analog signals from the load cell 3 and the ultrasonic emitter/receiver 6 are converted to digital form and stored. The distance from the ultrasonic emitter/receiver 6 and the ground is subtracted from the length of the penetrometer rod 2 to obtain the depth of penetration of the penetrometer cone into the ground. Other relevant information, such as the site identification, map coordinates, and the time and date of measurement may also be entered into the memory at this time. This digital information may later be transferred to a digital personal computer, which may be programmed to average and tabulate the field data as needed.

While the preferred embodiment of the invention has been illustrated and described in detail herein, it will be apparent that changes and additions may be made therein and thereto without departing from the spirit of the invention. Reference should, accordingly, be made to the appended claims in determining the true scope of the invention.

What is claimed is:

1. A cone penetrometer for determining the shear resistance of soil at different depths below the ground comprising:

(a) a penetrometer rod having a cone attached to its lower end;

(b) a load cell attached to the upper end of the penetrometer rod and providing an electrical signal output commensurate with the compressive force exerted upon the load cell;

(c) an ultrasonic emitter/receiver directing a high-frequency sound signal downwardly at the ground being penetrated and receiving a reflected sound signal therefrom, and providing an electrical signal output commensurate with the distance between the ultrasonic emitter/receiver and the ground;

(d) a data logger/processor having program and memory storage capacity in electrical communication with the load cell and the ultrasonic emitter/receiver and receiving from the load cell the electrical output commensurate with the distance between the ultrasonic emitter/receiver and the ground; storing these signals and retrieving the stored signals from the data logger/processor to a digital computer.

2. The cone penetrometer of claim 1 wherein the load cell provides an electrical voltage signal commensurate with the compressive force exerted upon the load cell.

3. The cone penetrometer of claim 1 wherein the ultrasonic emitter/receiver provides a current output signal commensurate with the distance between the ultrasonic emitter and the ground.

4. The cone penetrometer of claim 1 wherein the ultrasonic emitter/receiver provides a voltage output signal commensurate with the distance between the ultrasonic emitter and the ground.

5. The cone penetrometer of claim 1 wherein the data logger/processor converts the electrical output signals received from the load cell and the ultrasonic emitter/receiver to digital form.

6. The cone penetrometer of claim 1 wherein the data logger/processor has means for calculating the depth of penetration of the cone into the ground.

7. The cone penetrometer of claim 1 wherein the data logger/processor has means for transferring data stored therein to a digital computer.

8. A method of determining the shear resistance of soil comprising the steps of (a) forcing the cone and penetrometer rod of the penetrometer of claim 1 vertically downward into the ground; and (b) causing the load cell, the ultrasonic emitter/receiver, and the data logger/processor of claim 1 to record and store the compressive force exerted upon the load cell and the distance between the ultrasonic emitter/receiver and the ground.

9. The method of determining the shear resistance of soil of claim 8 further comprising the steps of (c) recording the site and the time of the measurement in the memory of the data logger/processor; and (d) transferring the data stored in the memory of the data logger/processor to a digital computer.

* * * * *